(12) United States Patent
Mule et al.

(10) Patent No.: US 7,482,148 B2
(45) Date of Patent: Jan. 27, 2009

(54) RECOMBINANT CALF-CHYMOSIN AND A PROCESS FOR PRODUCING THE SAME

(75) Inventors: Venkata Madhusudhan Reddy Mule, Hyderabad (IN); Padala Kamala Mythili, Hyderabad (IN); Karanam Gopalakrishna, Hyderabad (IN); Yamala Ramana, Hyderabad (IN); Donthi Reddy Bosu Reddy, Hyderabad (IN)

(73) Assignee: Sudershan Biotech Ltd., Andhra Pradesh (IN)

( * ) Notice: Subject to any disclaimer, the term of this patent is extended or adjusted under 35 U.S.C. 154(b) by 0 days.

(21) Appl. No.: 10/599,391

(22) PCT Filed: Mar. 30, 2004

(86) PCT No.: PCT/IN2004/000074

§ 371 (c)(1),
(2), (4) Date: Dec. 12, 2006

(87) PCT Pub. No.: WO2005/094185

PCT Pub. Date: Oct. 13, 2005

(65) Prior Publication Data

US 2007/0166785 A1 Jul. 19, 2007

(51) Int. Cl.
*C12N 9/50* (2006.01)
*C12N 15/59* (2006.01)
*C12N 15/70* (2006.01)
*C07K 1/14* (2006.01)
*C07K 1/30* (2006.01)

(52) U.S. Cl. .......... 435/226; 435/69.1; 435/252.33; 435/320.1; 530/412; 530/418; 536/23.2

(58) Field of Classification Search ............ None
See application file for complete search history.

(56) References Cited

U.S. PATENT DOCUMENTS

| | | | | | |
|---|---|---|---|---|---|
| 4,663,280 | A | * | 5/1987 | Sloma | 435/69.2 |
| 4,666,847 | A | * | 5/1987 | Alford et al. | 435/252.33 |
| 4,757,020 | A | * | 7/1988 | Beppu et al. | 435/252.33 |
| 4,935,370 | A | * | 6/1990 | Franke | 435/252.33 |
| 5,015,573 | A | * | 5/1991 | Yarranton et al. | 435/69.1 |
| 5,082,775 | A | * | 1/1992 | McCaman et al. | 435/69.7 |
| 5,434,067 | A | * | 7/1995 | Michaelis et al. | 435/196 |
| 5,496,711 | A | * | 3/1996 | Alford et al. | 435/69.1 |
| 5,525,484 | A | * | 6/1996 | Alford et al. | 435/69.1 |
| 5,593,865 | A | * | 1/1997 | Rudolph et al. | 435/69.1 |
| 5,650,554 | A | * | 7/1997 | Moloney | 800/288 |
| 5,766,599 | A | * | 6/1998 | Paoletti et al. | 424/199.1 |
| 5,917,018 | A | * | 6/1999 | Thøgersen et al. | 530/350 |
| 5,948,682 | A | * | 9/1999 | Moloney | 435/483 |
| 5,948,889 | A | * | 9/1999 | de Boer et al. | 530/350 |
| 5,955,297 | A | * | 9/1999 | Franke | 435/69.1 |
| 6,750,046 | B2 | * | 6/2004 | Moloney et al. | 435/69.7 |
| 6,753,167 | B2 | * | 6/2004 | Moloney et al. | 435/69.8 |
| 2004/0072320 | A1 | * | 4/2004 | Fahrenmark et al. | 435/226 |

FOREIGN PATENT DOCUMENTS

EP 0 077 109 * 4/1983

OTHER PUBLICATIONS

Emtage, J S, et al., 1983, "Synthesis of calf prochymosin (prorennin) in *Escherichia coli*", Proceedings of the National Academy of Sciences, USA, vol. 80, No. 12, pp. 3671-3675.*
McCaman, M T, et al., 1985, "Engineering of prochymosin alters its activation properties", Journal of Cellular Biochemistry, vol. 29, Suppl.9B, p. 134, Abstract 0755.*
McCaman, M T, et al., 1988, "Unusual zymogen-processing properties of a mutated form of prochymosin", Proteins: Structure, Function and Genetics, vol. 3, No. 4, pp. 256-261.*
Suzuki, J, et al., 1989, "Alteration of catalytic properties of chymosin by site-directed mutagenesis", Protein Engineering, vol. 2, No. 7, pp. 563-569.*
Suzuki, J, et al., 1990, "Site-directed mutagenesis reveals functional contribution of Thr218, Lys220 and Asp304 in chymosin", Protein Engineering, vol. 4, No. 1, pp. 69-71.*
Mantafounis, D. et al., 1990, "Protein engineering of chymosin; modification of the optimum pH of enzyme catalysis", Protein Engineering, vol. 3, No. 7, pp. 605-609.*
Strop, P, et al., 1990, "Engineering enzyme subsite specificity: preparation, kinetic characterization, and X-ray analysis at 2.0-angstrom resolution of Val111Phe site-mutated calf chymosin", Biochemistry, vol. 29, No. 42, pp. 9863-9871.*

(Continued)

*Primary Examiner*—Nashaat T. Nashed
*Assistant Examiner*—William W Moore
(74) *Attorney, Agent, or Firm*—Foley & Lardner LLP

(57) ABSTRACT

The present invention relates to a recombinant calf-Chymosin protein as set forth in SEQ ID No. 1; a recombinant calf-Chymosin gene as set forth in SEQ ID No. 2 encoding the protein comprising amino acid sequence of SEQ ID NO.1; an *E. coli* comprising the recombinant chymosin gene of SEQ ID No. 2; an expression vector pET21b comprising recombinant calf-chymosin gene as set forth in SEQ ID No. 2; and lastly a method for producing recombinant calf-chymosin protein as set forth in SEQ ID No. 1 which comprises steps of isolating calf-chymosin gene, cloning the same in bacterial expression vector pET21b, transforming said cloned vector into cells of *E. coli*, fermenting said *E. coli* to produce pro-chymosin, converting said pro-chymosin to chymosin and subsequently recovering the recombinant calf-chymosin.

14 Claims, No Drawings

OTHER PUBLICATIONS

Beppu, T, 1990, "Structure and function of milk-clotting aspartic proteinases", Protein Engineering, vol. 3, No. 4, pp. 304-305.*

Quinn, D, et al., 1991, "Modifying the substrate specificity of chymosin", Biochemical Society Transactions, vol. 19, No. 3, p. 267S.*

Huang, K, et al., 1992, "Functional implication of disulfide bond, CYS250-CYS283, in bovine chymosin", Biochemical and Biophysical Research Communications, vol. 187, No. 2, pp. 692-696.*

Pitts, J E, et al., 1993, "Expression and characterization of chymosin pH optima mutants produced in Trichoderma reesei, enzyme engineering of cattle chymosin", Journal of Biotechnology, vol. 8, No. 1, pp. 69-83.*

Yonezawa, M, et al., 1993, "Role of the amino-terminal amino acid sequences determining the in vitro refolding process of prochymosin polypeptide", Journal of Biotechnology, vol. 28, No. 1, 85-97.*

Nugent, P G, et al., 1996, "Protein engineering loops in aspartic proteinases: Site-directed mutagenesis, biochemical characterization and X-ray analysis of chymosin with a replaced loop from rhizopuspepsin", Protein Engineering, vol. 9, No. 10, pp. 885-893.*

Burton, S C, et al., "One step purification of chymosin by mixed mode chromatography", Biotechnology and Bioengineering, vol. 56, No. 1, pp. 45-55.*

Zhang, Y, et al., 1997, "Functional implications of disulfide bond, Cys45-Cys50, in recombinant prochymosin", Biochimica et Biophysica Acta, vol. 1343, No. 2, pp. 278-286.*

Albert, A, et al., 1998, "Protein engineering aspartic proteinases. Site-directed mutagenesis, biochemical characterisation, and X-ray analysis of chymosins with substituted single amino acid substitutions and loop replacements", Advances in Experimental Medicine and Biology, vol. 436, pp. 169-177.*

Li, H, et al., 1998, "Functional implications of the 21-24 loop in recombinant prochymosin", Biochimica et Biophysica Acta, vol. 1384, No. 1, pp. 121-129.*

Chitpinityol, S, et al., 1998, "Site-specific mutations of calf chymosin B which influence milk-clotting activity", Food Chemistry, vol. 62, No. 2, pp. 133-139.*

Chen, H, et al., 2000, "Functional implications of disulfide bond, Cys206-Cys210, in recombinant prochymosin", Biochemistry, vol. 39, No. 40, pp. 12140-12148.*

Zinovieva, N, et al., 2002, "Identification and characterization of multiple splicing forms of bovine prochymosin mRNA", Journal of Dairy Science, vol. 85, No. 12, pp. 3476-3479.*

* cited by examiner

SEQUENCE LISTING

```
<160> NUMBER OF SEQ ID NOS: 6

<210> SEQ ID NO 1
<211> LENGTH: 366
<212> TYPE: PRT
<213> ORGANISM: calf

<400> SEQUENCE: 1

Met Ala Ser Ile Thr Arg Ile Pro Leu Tyr Lys Gly Lys Ser Leu Arg
1               5                   10                  15

Lys Ala Leu Lys Glu His Gly Leu Leu Glu Asp Phe Leu Gln Lys Gln
                20                  25                  30

Gln Tyr Gly Ile Ser Ser Lys Tyr Ser Gly Phe Gly Glu Val Ala Ser
            35                  40                  45

Val Pro Leu Thr Asn Tyr Leu Asp Ser Gln Tyr Phe Gly Lys Ile Tyr
        50                  55                  60

Leu Gly Thr Pro Pro Gln Glu Phe Thr Val Leu Phe Asp Thr Gly Ser
65                  70                  75                  80

Ser Asp Phe Trp Val Pro Ser Ile Tyr Cys Lys Ser Asn Ala Cys Lys
                85                  90                  95

Asn His Gln Arg Phe Asp Pro Arg Lys Ser Ser Thr Phe Gln Asn Leu
            100                 105                 110

Gly Lys Pro Leu Ser Ile His Tyr Gly Thr Gly Ser Met Gln Gly Ile
        115                 120                 125

Leu Gly Tyr Asp Thr Val Thr Val Ser Asn Ile Val Asp Ile Gln Gln
    130                 135                 140

Thr Gly Gly Leu Ser Thr Gln Glu Pro Gly Asp Val Phe Thr Tyr Ala
145                 150                 155                 160

Glu Phe Asp Gly Ile Leu Gly Met Ala Tyr Pro Ser Leu Ala Ser Glu
                165                 170                 175

Tyr Ser Ile Pro Val Phe Asp Asn Met Met Asn Arg His Leu Val Ala
            180                 185                 190

Gln Asp Leu Phe Ser Val Tyr Met Asp Arg Asn Gly Gln Glu Ser Met
        195                 200                 205

Leu Thr Leu Gly Ala Ile Asp Pro Ser Tyr Tyr Thr Gly Ser Leu His
    210                 215                 220

Trp Val Pro Val Thr Val Gln Gln Tyr Trp Gln Phe Thr Val Asp Ser
225                 230                 235                 240

Val Thr Ile Ser Gly Val Val Val Ala Cys Glu Gly Gly Cys Gln Ala
                245                 250                 255

Ile Leu Asp Thr Gly Thr Ser Lys Leu Val Gly Pro Ser Ser Asp Ile
```

```
                    260              265              270
Leu Asn Ile Gln Gln Ala Ile Gly Ala Thr Gln Asn Gln Tyr Asp Glu
              275                280                285
Phe Asp Ile Asp Cys Asn Asn Leu Ser Tyr Met Pro Thr Val Val Phe
  290                295                300
Glu Ile Asn Gly Lys Met Tyr Pro Leu Thr Pro Ser Ala Tyr Thr Ser
305                310                315                320
Gln Asp Gln Gly Phe Cys Thr Ser Gly Phe Gln Ser Glu Asn His Ser
                  325                330                335
Gln Lys Trp Ile Leu Trp Asp Val Phe Ile Arg Glu Tyr Tyr Ser Val
              340                345                350
Phe Asp Arg Ala Asn Asn Leu Val Gly Leu Ala Lys Ala Ile
              355                360                365
```

<210> SEQ ID NO 2
<211> LENGTH: 1101
<212> TYPE: DNA
<213> ORGANISM: calf

<400> SEQUENCE: 2

```
atggctagca tcactaggat ccctctgtac aaaggcaagt ctctgaggaa ggcgctgaag      60
gagcatgggc ttctggagga cttcctgcag aaacagcagt atggcatcag cagcaagtac     120
tccggcttcg gggaggtggc cagcgtgccc ctgaccaact acctggatag tcagtacttt     180
gggaagatct acctcgggac cccgccccag gagttcaccg tgctgtttga cactggctcc     240
tctgacttct gggtaccctc tatctactgc aagagcaatg cctgcaaaaa ccaccagcgc     300
tcgaccccga aaagtcgtc caccttccag aacctgggca agccccctgtc tatccactac     360
gggacaggca gcatgcaggg catcctgggc tatgacaccg tcactgtctc caacattgtg     420
gacatccagc agacaggagg cctgagcacc caggagcccg ggacgtcctt cacctatgcc     480
gaattcgacg ggatcctggg gatggcctac ccctcgctcg cctcagagta ctcgataccc     540
gtgtttgaca catgatgaa caggcacctg gtggcccaag acctgttctc ggtttacatg     600
gacaggaatg ccaggagag catgctcacg ttgggggcca tcgacccgtc ctactacaca     660
gggtccctgc actgggtgcc cgtgacagtc agcagtact ggcagttcac tgtggacagt     720
gtcaccatca gcggtgtggt tgtggcctgt gagggtggct gtcaggccat cctggacacg     780
ggcacctcca gctggtcgg gcccagcagc gacatcctca catccagca ggccattgga     840
gccacacaga accagtacga tgagtttgac atcgactgca caacctgag ctacatgccc     900
actgtggtct ttgagatcaa tgccaaaatg tacccactga ccccctccgc ctataccagc     960
caggaccagg gcttctgtac cagtggcttc cagagtgaaa tcattccca gaatggcatc    1020
ctgtgggatg ttttcatccg agagtattac agcgtctttg acagggccaa caacctcgtg    1080
gggctggcca agccatctg a                                                1101
```

<210> SEQ ID NO 3
<211> LENGTH: 25
<212> TYPE: DNA
<213> ORGANISM: Artificial Sequence
<220> FEATURE:
<223> OTHER INFORMATION: reverse primer for amplification of prepro chymosin

<400> SEQUENCE: 3

```
tgtggggaca gtgaggttct tggtc                                             25
```

```
<210> SEQ ID NO 4
<211> LENGTH: 24
<212> TYPE: DNA
<213> ORGANISM: Artificial Sequence
<220> FEATURE:
<223> OTHER INFORMATION: forward primer for amplification of prepro
      chymosin

<400> SEQUENCE: 4
atgaggtgtc tcgtggtgct actt                                              24

<210> SEQ ID NO 5
<211> LENGTH: 39
<212> TYPE: DNA
<213> ORGANISM: Artificial Sequence
<220> FEATURE:
<223> OTHER INFORMATION: forward primer containing Nde I site

<400> SEQUENCE: 5
gatatacata tggctagcat cactaggatc cctctgtac                              39

<210> SEQ ID NO 6
<211> LENGTH: 34
<212> TYPE: DNA
<213> ORGANISM: Artificial Sequence
<220> FEATURE:
<223> OTHER INFORMATION: reverse primer containing Hind III site

<400> SEQUENCE: 6
gcagtaagct tgacagtgag gttcttggtc agcg                                   34
```

RECOMBINANT CALF-CHYMOSIN AND A PROCESS FOR PRODUCING THE SAME

FIELD OF THE INVENTION

The present invention relates to recombinant calf-chymosin and a process for producing the same.

BACKGROUND OF THE INVENTION

Chymosin is an enzyme which is particularly useful in the preparation of cheese. Natural sources of chymosin include stomachs of calf, goat, lamb, porcine and the like. However, commercial chymosin is primarily obtained from the fourth stomach of milk fed calves. Alternate sources of chymosin have been developed particularly because of the decrease in calf production. Production and extraction of commercially valuable proteins from recombinant microorganisms encouraged the study of producing and purifying microbially produced chymosin. However, a process suitable for commercial scale production and recovery of chymosin has not been developed so far.

OBJECTS OF THE INVENTION

The main object of the present invention is to produce recombinant calf-chymosin, an enzyme particularly useful in the preparation of cheese.

Yet another main object of the present invention is to isolate the chymosin gene from calf tissues.

Still another main object of the present invention is to clone the chymosin gene in a bacterial expression vector.

Still another main object of the present invention is to express the recombinant calf-chymosin in *E. coli* cell.

Still another main object of the present invention is to provide an efficient process for expressing prochymosin gene and its conversion into enzymatically active pure chymosin.

STATEMENT OF THE PRESENT INVENTION

The present invention relates to a recombinant calf-Chymosin protein as set forth in SEQ ID No. 1; a recombinant calf-Chymosin gene as set forth in SEQ ID No. 2 encoding the protein comprising amino acid sequence of SEQ ID NO.1; an *E. coli* comprising the recombinant calf-chymosin gene of SEQ ID No. 2; an expression vector pET21b comprising recombinant calf-chymosin gene as set forth in SEQ ID No. 2; and lastly a method for producing recombinant calf-chymosin protein as set forth in SEQ ID No. 1 which comprises steps of isolating calf-chymosin gene, cloning the same in bacterial expression vector pET21b, transforming said cloned vector into cells of *E. coli,* fermenting said *E. coli* to produce pro-chymosin, converting said pro-chymosin to chymosin and subsequently recovering the recombinant calf-chymosin.

DETAILED DESCRIPTION OF THE INVENTION

The present invention relates to a recombinant calf-Chymosin protein as set forth in SEQ ID No. 1.

In yet another embodiment of the present invention, the protein comprising amino acid sequence of SEQ ID No.1 is encoded by a recombinant calf-chymosin gene as set forth in SEQ ID No.2.

In still another embodiment of the present invention, an *E. coli* comprising the recombinant calf-chymosin gene of SEQ ID No. 2.

In still another embodiment of the present invention *E. coli* cells are BL21 cells.

In still another embodiment of the present invention, an expression vector pET21b comprising recombinant calf-chymosin gene as set forth in SEQ ID No. 2.

In still another embodiment of the present invention a method for producing recombinant calf-chymosin protein as set forth in SEQ ID No. 1 which comprises steps of isolating calf-chymosin gene, cloning the same in bacterial expression vector pET21b, transforming said cloned vector into cells of *E. coli,* fermenting said *E. coli* to produce pro-chymosin, converting said pro-chymosin to chymosin and subsequently recovering the recombinant calf-chymosin.

In still another embodiment of the present invention, the calf-chymosin gene is obtained by isolating RNA from fourth stomach of calf tissue, synthesising a first strand of cDNA therefrom by treating the same with a reverse primer of SEQ ID NO.3 and then with a forward primer of SEQ ID NO.4.

In still another embodiment of the present invention the cDNA is ligated at smaI site of pBSSK+ plasmid and then transformed into TOP10 cells of *E-coli.*

In still another embodiment of the present invention recombinant clones were identified and treated with a forward primer of SEQ ID NO.5 and reverse primer of SEQ ID NO.6 containing Nde I and Hind III sites to obtain an amplified fragment.

In still another embodiment of the present invention the amplified fragment is transformed into cells of *E. coli* for expressing chymosin gene.

In still another embodiment of the present invention *E. coli* cells containing recombinant calf-chymosin gene is fermented, the suspended cells produced on completion of fermentation are lysed, chilled and pH adjusted to about 8 before incubation at room temperature and the separation of supernatant containing prochymosin.

In still another embodiment of the present invention the pH of supernatent is adjusted to about 2 for activation, further incubated for about 6 hrs and subjected to filtration to obtain filtrate.

In still another embodiment of the present invention the filtrate is subjected to sodium chloride precipitation, then the precipitate is dissolved followed by the addition of sodium benzoate as preservative.

In the instant invention, Calf-chymosin gene is isolated preferably from the fourth stomach of milk fed calf tissues. Recombinant calf-chymosin is produced by cloning chymosin gene with bacterial expression vector pET21b and is transformed into *E-coli* strain. This *E-coli* strain containing recombinant calf-chymosin gene is fermented under suitable conditions preferably in a culture medium developed by us. This medium contains the following Peptone—12 g/l Yeast Extract—24 g/l Sodium chloride—10 g/l Prochymosin produced during fermentation is subjected to denaturation by increasing the pH of the medium to 10-11. The suspension then diluted and the pH reduced to about 8 for effective renaturation of the protein. The prochymosin thus obtained is then acidified for activation and is further processed.

This invention relates to a process for producing recombinant calf-chymosin which comprises the steps of isolating calf-chymosin gene, cloning the same in bacterial expression vector pET21b, transforming said cloned vector into cells of *E-coli,* fermenting said *E-coli* strains to produce pro-chymosin, converting said pro-chymosin to chymosin and subsequently recovering the recombinant calf-chymosin. This invention also includes recombinant calf-chymosin having the following amino acid sequence as set forth in SEQ ID No. 1 and the corresponding gene sequence as set forth in SEQ ID No. 2.

SEQ ID No. 1. Recombinant Calf-Chymosin Protein Sequence

Met A S I T R I P L Y K G K S L R K A L K E H G L L E D F L Q K Q Q Y G I S S K
Y S G F G E V A S V P L T N Y L D S Q Y F G K I Y L G T P P Q E F T V L F D T G
S S D F W V P S I Y C K S N A C K N H Q R F D P R K S S T F Q N L G K P L S I H
Y G T G S M Q G I L G Y D T V T V S N I V D I Q Q T G G L S T Q E P G D V F T Y
A E F D G I L G M A Y P S L A S E Y S I P V F D N M M N R H L V A Q D L F S V
Y M D R N G Q E S M L T L G A I D P S Y Y T G S L H W V P V T V Q Q Y W Q F
T V D S V T I S G V V V A C E G G C Q A I L D T G T S K L V G P S S D I L N I Q
Q A I G A T Q N Q Y D E F D I D C N N L S Y M P T V V F E I N G K M Y P L T P S
A Y T S Q D Q G F C T S G F Q S E N H S Q K W I L W D V F I R E Y Y S V F D R
A N N L V G L A K A I Stop

SEQ ID No. 2. Recombinant Calf-Chymosin Gene Sequence

ATG GCT AGC ATC ACT AGG ATC CCT CTG TAC AAA GGC AAG TCT CTG
AGG AAG GCG CTG AAG GAG CAT GGG CTT CTG GAG GAG TTC CTG CAG
AAA CAG CAG TAT GGC ATC AGC AGC AAG TAC TCC GGC TTC GGG GAG
GTG GCC AGC GTG CCC CTG ACC AAC TAC CTG GAT AGT CAG TAC TTT
GGG AAG ATC TAC CTC GGG ACC CCG CCC CAG GAG TTC ACC GTG CTG
TTT GAC ACT GGC TCC TCT GAC TTC TGG GTA CCC TCT ATC TAC TGC AAG
AGC AAT GCC TGC AAA AAC CAC CAG CGC TTC GAC CCG AGA AAG TCG
TCC ACC TTC CAG AAC CTG GGC AAG CCC CTG TCT ATC CAC TAC GGG
ACA GGC AGC ATG CAG GGC ATC CTG GGC TAT GAC ACC GTC ACT GTC
TCC AAC ATT GTG GAC ATC CAG CAG ACA GGA GGC CTG AGC ACC CAG
GAG CCC GGG GAC GTC TTC ACC TAT GCC GAA TTC GAC GGG ATC CTG
GGG ATG GCC TAC CCC TCG CTC GCC TCA GAG TAC TCG ATA CCC GTG
TTT GAC AAC ATG ATG AAC AGG CAC CTG GTG GCC CAA GAC CTG TTC
TCG GTT TAC ATG GAC AGG AAT GGC CAG GAG AGC ATG CTC ACG TTG
GGG GCC ATC GAC CCG TCC TAC TAC ACA GGG TCC CTG CAC TGG GTG
CCC GTG ACA GTG CAG CAG TAC TGG CAG TTC ACT GTG GAC AGT GTC
ACC ATC AGC GGT GTG GTT GTG GCC TGT GAG GGT GGC TGT CAG GCC
ATC CTG GAC ACG GGC ACC TCC AAG CTG GTC GGG CCC AGC AGC GAC
ATC CTC AAC ATC CAG CAG GCC ATT GGA GCC ACA CAG AAC CAG TAC
GAT GAG TTT GAC ATC GAC TGC AAC AAC CTG AGC TAC ATG CCC ACT
GTG GTC TTT GAG ATC AAT GGC AAA ATG TAC CCA CTG ACC CCC TCC
GCC TAT ACC AGC CAG GAC CAG GGC TTC TGT ACC AGT GGC TTC CAG
AGT GAA AAT CAT TCC CAG AAA TGG ATC CTG TGG GAT GTT TTC ATC
CGA GAG TAT TAC AGC GTC TTT GAC AGG GCC AAC AAC CTC GTG GGG
CTG GCC AAA GCC ATC TGA

In the above sequence, amino acids shown in red indicate sequence variation of chymosin gene of our invention compared to the reported and published sequence.

A recombinant calf-Chymosin protein is set forth in SEQ ID No. 1, wherein the replacement of single amino acid Aspartic Acid (D) with Glycine (G) at position 287 is also covered and is referred to as SEQ ID No. 1.

A recombinant calf-Chymosin gene is set forth in SEQ ID No. 2, wherein the replacement of nucleotide GAT with GCC at position 287 is also covered and is referred to as SEQ ID No.2.

The invention is further elaborated with the help of following examples. However, these examples should not be construed to limit the scope of the invention.

EXAMPLES

Example 1

Isolation of Calf-chymosin Gene

Total RNA was isolated from the 4$^{th}$ stomach of calf tissue. The tissue was frozen and ground to a fine powder. The powder was transferred to a 50 ml centrifuge tube containing 10 ml of denaturing buffer (4M Guanidine thiocyanate, 25 mM Sodium citrate pH 7.0, 0.5% Sarkosyl and 0.1M 2-Mercaptoethanol). To this 1 ml of 2M Sodium acetate pH 4.0, 10 ml of Phenol and 2 ml of Chloroform were added and kept on ice for 20 min. Later, it was centrifuged for 15 min at 12,000 rpm, 4° C. The upper aqueous phase was transferred carefully into a new tube to which an equal volume of isopropanol was added and kept at −20° C. for 1 hr. The RNA was precipitated at 15,000 rpm for 15 min. at 4° C. The RNA pellet was washed with 70% ethanol and dissolved in 1 ml of denaturing buffer followed by two successive extractions with phenol:chloroform:isoamyl alcohol (30:29:1). The RNA was precipitated with ⅒ volume of 3M sodium acetate (pH 5.2) and 2.5 volume of ethanol and dissolved in 500 μl of DEPC treated water.

For the synthesis of first strand of the cDNA, 10 μg of RNA was dissolved in 16 μl DEPC water and the following components were added: 2 μl of 10 mM dNTP mix, 2 μl of 1 μg of reverse primer (5'-TGT GGG GAC AGT GAG GTT CTT GGT C-3'), 4 μl of 10×RT buffer (200 mM Tris-HCl, pH 8.4, 500 mM KCl), 8 μl of 25 mM MgCl2, 4 μl of 0.1M DTT, 2 μl of Rnase inhibitor, 2 μl (50 units) of Superscript II reverse transcriptase. The mixture was incubated for 50 min at 42° C. and the reaction is stopped by inactivating the enzyme at 70° C. for 15 min. PCR amplification of prepro chymosin was performed using the 50 ng of 1st strand cDNA with a reverse primer (5'-TGT GGG GAC AGT GAG GTT CTT GGT C-3'), and a forward primer (5'-ATG AGG TGT CTC GTG GTG CTA CTT-3') in a thermal cycler programmed as (step 1: 95° C.-5'; step 2: 94° C.-30 sec; step 3: 54° C.-30 sec; step 4: 72° C.-1 min; step 5: go to step 2 34 times; step 6: 72° C.-7 min; step 7: end). The PCT reaction when analyzed on 1.0% agarose gel showed an amplified band of 1.2 kb. The 1.2 kb fragment was cut with a sterile blade and the gel slice was dissolved in 500 μl of Tris saturated phenol and left in liquid nitrogen for a few min. The microcentrifuge tube was allowed to come to room temperature and centrifuged for 5 min at 12,000 rpm, 4° C. The upper aqueous phase was extracted with phenol:chloroform:isoamyl alcohol (25:24:1) and DNA was precipitated with ⅒th volume sodium acetate and 2.5 volume ethanol at −70° C. for 1 h. DNA was precipitated at 15,000 rpm for 15 min. The pellet was dried and dissolved in sterile distilled water. This eluted 1.2 kb fragment was ligated at SmaI site of pBSSK+ plasmid, which was then transformed in to TOP10 cells of E. coli. The recombinant clones were selected (blue white screening) and checked with restriction digestion analysis of the plasmids. Recombinant plasmid was taken as a template and a PCR was performed using a forward primer (5'-GAT ATA CAT ATG GCT AGC ATC ACT AGG ATC CCT CTG TAC-3') and reverse primer (5'-GCA GTA AGC TTG ACA GTG AGG TTC TTG GTC AGC G-3') containing Nde I and Hind III sites. An amplified band of 1098 bp was observed when the PCR product was analyzed on 1.0% agarose gel. This amplified fragment of 1098 bp was eluted from the gel and ligated in pET21b expression vector at Nde I and Hind III sites and transformed in to BL21 cells of E. coli for the expression of the chymosin gene.

Example 2

Fermentation of Recombinant E. coli Expressing Calf-chymosin

Fermentation of E. coli cells containing recombinant calf-chymosin gene was carried out in 15 L fermentor with 6 L of working volume. Fermentation was carried out in SBL medium as herein after described using 4% inoculum as seed. The fermentation process lasts for 22-24 h., and the whole procedure can be divided into four stages:
Stage 1: Preparation of SBL media.
Stage 2: Preparation of Accessories for fermentation.
Stage 3: Preparation of Seed.
Stage 4: Process of Fermentation.

Composition of the SBL medium:
Peptone: 12 g/L
Yeast Extract: 0.24 g/L
Sodium Chloride: 10 g/L These ingredients were calculated for 6 L, weighed and dissolved in 5.75 L of distilled water and later volume was made up to 6L with water, pH was set to 7.0 using 4N NaOH. 240 ml was separated out from 6L and was autoclaved separately at 15 lb/sq.inch for 20 min. The remaining 5.76 L was taken in fermentor vessel, 1 ml of sigma A concentrate antifoam was added and autoclaved with the vessel at 15 lb/sq.inch for 45 min.

Example 3

Preparation of Supplements for Fermentation

1. Lactose: 0.4% (w/v) lactose for 6L medium was prepared by dissolving 24 g in 150 ml distilled water, autoclaved at 15 lb/sq.inch for 20 min. 0.2% (w/v) lactose for 6L medium was prepared by dissolving 12 g in 150 ml distilled water, autoclaved at 15 lb/sq.inch for 20 min.

2. Glycerol: 0.3% (w/v) Glycerol for 6 L medium was made by adding 18 ml of glycerol to 82 ml of water, autoclaved at 15 lb/sq.inch for 20 min.

3. Ampicillin: 100 mg/ml ampicillin was made by dissolving 1200 mg of sodium salt of ampicillin in 12 ml distilled water. The solution was filter sterilized by passing through 0.2 microns millipore syringe filter.

4. IPTG (Isopropyl-β-D-thiogalactopyranoside): 2 mM IPTG (for 6L medium) was prepared by dissolving 2.85 g of IPTG in 20 ml distilled water. The solution was filter sterilized by passing through 0.2 microns millipore syringe filter.

5. 4N NaOH: 100 ml of 4N NaOH was made by dissolving 16 g of NaOH pellets in 90 ml of autoclaved water, and after dissolution, volume is made up to 100 ml with water.

Example 4

Preparation of Seed

4% SBL medium (240 ml of 6L medium) was inoculated with 100 μl glycerol stock of *E. coli* cells in 500 ml baffled flask containing 100 μg/ml ampicillin. The flask was kept shaking at 37° C., 250 rpm for 18 h. Optical Density (OD) of the culture was read at 600 nm in Shimadzu Spectrophotometer.

Example 5

Fermentation Process

The whole process of fermentation begins with inoculation of seed at 4% into SBL medium. The pre-grown seed is inoculated into 5.76 L autoclaved SBL medium. Along with the seed −0.3% glycerol, 6 ml of 100 μg/ml ampicillin were also added through the inlet pump. Prior to addition of seed, the fermentor was made ready by calibrating different probes like pH probe, DO probe and Temperature probe.
a) pH probe calibration: pH probe was calibrated using standard pH 4.0 and pH 7.0 solutions.
b) Dissolved Oxygen (DO) probe calibration: DO probe was calibrated by using 5% sodium nitrite solution for 0% DO.
c) Temperature probe calibration: Temperature probe was checked using water at different temperatures in a standard water bath.

Fermentation conditions: The fermentation parameters set were given as below, and the fermentation was started by quick addition of the seed into the inoculation port.

| | |
|---|---|
| Temperature | 37° C. |
| pH | 7.0, |
| Agitation | 350 RPM, |
| Dissolved Oxygen | 30% |
| SLPM | 1.25 |
| VVM | 0.2 |

After 2 h of inoculation 6 ml of 100 μg/ml ampicillin was added. When OD (at 600 nm) reaches about 4-5 (after 3 h.) 0.4% Lactose was added. Then the temperature was reduced to 32° C. When OD reaches 7-8 (after 5 h.) 0.2% Lactose was added. Agitation speed was then increased to 450 rpm. When the OD (at 600 nm) reaches 10.0, the culture batch was induced with 2 mM IPTG.

pH monitoring during the fermentation process: pH was monitored carefully during the process of fermentation from the seed inoculation stage till the end. Initially during the growth phase of bacteria the pH of the culture drops, and the pH is maintained at 7.0 using 4N NaOH. After substantial growth of bacteria, pH shoots above 7.0 and addition of 4N NaOH was completely stopped. Samples of 1 ml were collected from the fermentor at different time points, viz., uninduced (immediately before IPTG addition), 3 h., 6 h., and 9 h, after IPTG addition, and were processed for loading onto the gel for SDS-PAGE analysis.

Cell harvesting: After running the fermentor for 20 to 24 h following seed inoculation, and when the OD (at 600 nm) of the fermentor sample reads to ~20 O.D/ml, the fermentor batch was terminated by switching off all the controls.

Pelleting and storage of the cells: After termination of the batch, the cell culture was pelleted by centrifuging at 8000×g for 10 min. Supernatant was discarded and the pellet was stored in −70° C. freezer until further use.

Extraction and purification of chymosin enzyme:

*E. coli* cells after fermentation were suspended in 3.5 to 4 volumes of 10 mM EDTA (pre-chilled, 4° C.) and the suspension was incubated at 4° C. for 30 to 60 min to obtain homogeneous suspension. Later the suspension was subjected to lysis by adding equal volume of alkali solution (0.2 N Sodium hydroxide) to a final concentration of 0.1 N with continuous stirring for 15-20 min at 4° C. For complete denaturation and effective renaturation in the subsequent step, the lysed suspension was diluted to 9-12 folds with pre-chilled (4° C.) aqueous solution (H2O). Diluted suspension was allowed to stand at 4° C. for 30 min and the pH was readjusted to 8.0 by addition of 1.0 M glycine solution to a final concentration of 56 mM and allowed to stand at 4° C. for 30 min. The inactive form-pro-chymosin at this stage was incubated for 72 h at RT (28±2° C.) for proper refolding.

During this incubation period, the cell debris and other solid masses (Nucleic acid complexes) settles to the bottom and the supernatant can be decanted to obtain clear folded pro-chymosin.

In the subsequent steps the pH of pro-chymosin was adjusted to 2.0 for the activation. The adjustment is mainly by addition of a buffer with pH 1.5 (1.0M Hydrochloric acid and 1.0M glycine in 0.8:1.0-ratio). The extract was kept at low pH for a period of 6-8 h. Following the above activation, the crude low pH extract was subjected to a step where by precipitated impurities can be separated. This separation can be achieved by conventional industrial separation methods such as filtration (Whatmann No. 3). Hence, the process is economically efficient, can be easily scaled up for commercial production.

The supernatant or filtrate resulting from the above separation containing the extracted milk clotting enzyme can be processed in any one of the three methods. In method I the enzyme was concentrated by subjecting to sodium chloride precipitation to about 5.8-6.0 M. Precipitation was usually carried at 4° C. by gradual addition of the required amount of salt and subjecting to continuous stirring for an hour after complete addition of the salt. The solution was then subjected to vacuum filtration using 0.2 micron nylon membranes and the supernatant free of any enzyme can be discarded. The wet precipitate was resuspended in a 4.0 pH buffer and subsequently increased to pH 5.0 and formulated for stability.

In Method II, the pH of the filtrate was increased to the pH (to 4.7; or to 5.0) and the same was maintained at 32° C. for about an hour and subjected to another filtration to obtain clear chymosin. However, the higher pH ranges around 5.0 are not preferred, which may reduce the stability of the enzyme during storage might be due to the exposure of the active site during the process. Hence, the preferred method of activation is the acidification followed by precipitation.

In Method III, after acidification step the pH of the filtrate was increased to 4.7 and subjected to sodium chloride precipitation. The precipitate was dissolved as mentioned in Method I. The chymosin produced in all the above three methods is substantially pure, needs to be formulated to the desired specifications for final use. The salt concentration for formulation (NaCl) was brought to about 10% and a preservative such as Sodium benzoate was added. The enzymatic strengths were measured in terms of IMCU (International Milk Clotting Units). In the present investigation, 6000-9000 IMCU per gram of biomass was obtained.

Solutions and reagents required for chymosin process:

| | |
|---|---|
| Solution A: | 0.01M EDTA |
| Solution B: | 0.2N Sodium hydroxide |
| Solution C: | Autoclaved water |
| Solution D: | 1.0M Glycine |
| Solution E: | I) Solution D |
| | II) 1.0N Hydrochloric acid |
| | Mix (I) and (II) in 1:0.8 ratio and pH should be 1.5 |
| Solution F: | 5.0M Sodium chloride |
| Solution G: | I) Solution D |
| | II) 0.5N Sodium hydroxide |
| | Mix (I) and (II) in 1:0.4 ratio and should be pH 9.5 |
| Reagent H: | Sodium benzoate |
| Reagent I: | Sodium chloride |
| Solution J: | 0.2M Glycine with 0.001M EDTA. |
| Solution J: | Adjust the pH of solution J to 4.0 with Solution E. |
| Solution J: | Adjust the pH of solution J to 5.0 with Solution E. |
| Reagent K: | Trehalose-filter sterilized solution (10%). |

The invention claimed is:

1. An isolated recombinant calf-Chymosin protein having the amino acid sequence set forth in SEQ ID NO:1.

2. An isolated recombinant calf-Chymosin gene comprising the nucleic acid sequence set forth in SEQ ID NO:2.

3. The recombinant calf-chymosin gene of claim 2 consisting of the nucleic acid sequence of SEQ ID NO:2 encoding the amino acid sequence of SEQ ID NO:1.

4. An *E. coli* cell comprising the recombinant chymosin gene of SEQ ID NO:2.

5. The *E. coli* of claim 4 which is a BL21 cell of *E. coli*.

6. An expression vector pET21b comprising the recombinant calf-chymosin gene as set forth in SEQ ID NO:2.

7. A method for producing the recombinant calf-chymosin protein as set forth in SEQ ID NO:1 which comprises the steps of
  (i) isolating a calf-chymosin gene encoding the calf-chymosin protein of SEQ ID NO:1,
  (ii) cloning said gene in the bacterial expression vector pET21b,
  (iii) transforming said cloned vector into cells of *E. coli*,
  (iv) fermenting said *E. coli* to produce pro-chymosin,
  (v) converting said pro-chymosin to chymosin and
  (vi) subsequently recovering the recombinant calf chymosin.

8. The method of claim 7, wherein the calf-chymosin gene is obtained by (i) isolating RNA from the fourth stomach of a calf and (ii) synthesizing a first strand of cDNA therefrom by treating the RNA with a reverse primer of SEQ ID NO:3 and with a forward primer of SEQ ID NO:4.

9. The method of claim 8, wherein the eDNA is ligated at the SmaI site of the pBSSK+ plasmid and then transformed into TOP10 cells of *E. coli*.

10. The method of claim 9, wherein said recombinant clones were identified and treated with a forward primer of SEQ ID NO:5 and reverse primer of SEQ ID NO:6 containing NdeI and HindIII sites to obtain an amplified fragment.

11. The method of claim 10, wherein the amplified fragment is transformed into cells of *E. coli* for expressing the chymosin gene.

12. The method of claim 11, wherein *E. coli* cells containing recombinant calf-chymosin gene is fermented, the suspended cells produced on completion of fermentation are lysed, chilled and pH adjusted to about 8 before incubation at room temperature and the separation of supernatent containing prochymosin.

13. The method of claim 12, wherein
  (i) the pH of the supernatant is adjusted to about pH 2 for activation,
  (ii) the supernatant is further incubated for about 6 hrs, and
  (iii) then subjected to filtration to obtain a filtrate.

14. The method of claim 13, wherein
  (i) the filtrate is subjected to sodium chloride precipitation,
  (ii) the resulting precipitate is dissolved and
  (iii) sodium benzoate is added as preservative.

* * * * *

UNITED STATES PATENT AND TRADEMARK OFFICE
CERTIFICATE OF CORRECTION

Page 1 of 1

PATENT NO. : 7,482,148 B2
APPLICATION NO. : 10/599391
DATED : January 27, 2009
INVENTOR(S) : Mule et al.

It is certified that error appears in the above-identified patent and that said Letters Patent is hereby corrected as shown below:

ON THE COVER PAGE

Item (22) should read:

-- (22)   Filed: Sep. 27, 2006 --

Please remove Items (86) and (87).

Signed and Sealed this
Twenty-third Day of August, 2011

David J. Kappos
*Director of the United States Patent and Trademark Office*